(12) United States Patent
Kane et al.

(10) Patent No.: US 8,596,861 B2
(45) Date of Patent: Dec. 3, 2013

(54) METHOD AND SYSTEM FOR DETECTING CORROSION UNDER INSULATION

(75) Inventors: Russell D. Kane, Houston, TX (US); Isaac Cohen, Minnetonka, MN (US); Roland Mieszianko, Plymouth, MN (US); David A. Eden, Spring, TX (US)

(73) Assignee: Honeywell International Inc, Morristown, NJ (US)

( * ) Notice: Subject to any disclaimer, the term of this patent is extended or adjusted under 35 U.S.C. 154(b) by 576 days.

(21) Appl. No.: 12/265,977

(22) Filed: Nov. 6, 2008

(65) Prior Publication Data
US 2010/0107767 A1     May 6, 2010

(51) Int. Cl.
*G01N 25/00* (2006.01)
*G01J 5/00* (2006.01)
*G01K 3/00* (2006.01)

(52) U.S. Cl.
USPC ........ 374/5; 374/4; 374/7; 374/121; 374/141; 374/137

(58) Field of Classification Search
USPC ............ 374/5, 4, 7, 121, 141, 124, 137
See application file for complete search history.

(56) References Cited

U.S. PATENT DOCUMENTS

| 4,647,220 | A | * | 3/1987 | Adams et al. | 374/5 |
| 5,376,793 | A | * | 12/1994 | Lesniak | 250/341.6 |
| 5,582,485 | A | * | 12/1996 | Lesniak | 374/5 |
| 6,495,833 | B1 | * | 12/2002 | Alfano et al. | 250/341.8 |
| 6,712,502 | B2 | * | 3/2004 | Zalameda et al. | 374/5 |
| H2127 | H | * | 10/2005 | Byrd | 374/121 |
| 8,289,372 | B2 | * | 10/2012 | Hamrelius et al. | 348/32 |
| 2005/0111520 | A1 | * | 5/2005 | Ignatowicz | 374/120 |
| 2005/0135546 | A1 | | 6/2005 | Ponstingl et al. | |
| 2005/0207468 | A1 | * | 9/2005 | McCullough et al. | 374/5 |
| 2008/0107147 | A1 | * | 5/2008 | Kollgaard et al. | 374/5 |
| 2009/0312956 | A1 | * | 12/2009 | Zombo et al. | 702/34 |

FOREIGN PATENT DOCUMENTS

KR     10-2004-0041243 A     5/2004

OTHER PUBLICATIONS

Ong, P. S. et al., "Quantitative Characterization of Corrosion Under Insultation," *Journal of Nondestructive Evaluation* (1997) 16(3):135-146.
PCT International Search Report for PCT/US2009/062449 dated Jun. 8, 2010.

* cited by examiner

*Primary Examiner* — Mirellys Jagan
(74) *Attorney, Agent, or Firm* — Luis M. Ortiz; Kermit D. Lopez; Ortiz & Lopez, PLLC

(57) ABSTRACT

The present invention relates generally to thermal imaging systems and methods and uses therefor, and in a particular though non-limiting embodiment, to a method of detecting corrosion under insulation, as well as corrosion-related material data associated therewith. The system utilizes advanced infrared imaging video cameras to detect characteristic signatures of wet thermal traits on process equipment. Various embodiments of the invention integrate equipment, automation, and algorithms to form a method for identifying wet thermal insulation by scanning multiple locations along insulated piping, tanks, or other manufacturing equipment. Such scans can occur individually, sequentially, or simultaneously, with the results then being stored and comparatively analyzed. Further embodiments comprise tracking the approximate time of exposure to moisture, prediction of the corrosion rates for underlying insulated metal substrates, and measuring wall thicknesses along either predetermined random portions of the metal substrate.

20 Claims, 2 Drawing Sheets

METHOD AND SYSTEM FOR DETECTING CORROSION UNDER INSULATION

FIELD OF THE INVENTION

The present invention relates generally to thermal imaging systems and methods and uses therefor, and in a particular though non-limiting embodiment, to a method of detecting corrosion under insulation, as well as corrosion-related material data associated therewith.

BACKGROUND OF THE INVENTION

Corrosion under insulation (CUI) is corrosion that develops over time beneath thermal insulation used on pipes, tanks and other manufacturing and process equipment. Wherever piping, tanks or equipment are thermally insulated, there is potential for CUI. It is usually caused by condensation, rainwater, cleaning fluids, etc., that permeate into the insulation and attack the substrate to which it is applied. Impurities in the atmosphere and temperature gradients between tubulars and associated insulation also play a role in CUI development. Temperature gradients at the metal surface can lead to concentration of corrosive species, for example salts, which will accelerate the corrosion attack. Regardless of how securely insulation materials are applied to a substrate material, there will inevitably be areas where fluids can seep in, and where temperature gradients exist, thereby creating conditions that subsequently causes corrosion and damage to the substrate.

Detection of CUI in industrial plants has been identified as a significant problem, which can affect the integrity of tanks and pipes and lead to a shortening of the lifespan or even outright failure of expensive industrial infrastructure. Lengthy inspections and equipment failures often lead to manufacturing facility downtime, and consequently a loss of efficiency and increase in associated costs. CUI can be especially problematic wherever mastic is used as a finish, as well as around seals and metal ductwork, and wherever prior mechanical damage has occurred. As a consequence of CUI damage, a complete substrate replacement can ultimately become necessary.

One insidious aspect of CUI is that the corrosion is hidden from view by the thermal insulation. Typically, plants have miles of piping and thousands of square feet of insulation covered equipment. It is neither practical nor economical to remove the insulation at all locations for direct inspection. Traditionally, assessment of CUI has been handled manually using simple hand-held thermal imaging cameras to identify locations of wet thermal insulation. However, the accuracy of this equipment has been insufficient and costly due to "false calls," which result in added expense due to the downtime associated with unnecessary removal and inspection of thermal insulation.

There is, therefore, a widespread but presently unmet need for an efficient and accurate detection system capable of identifying likely CUI corrosion sites in a variety of industrial manufacturing and processing environments.

SUMMARY OF THE INVENTION

A method of detecting corrosion under insulation is provided, the method including at least the steps of: disposing one or more thermal imaging devices in electromagnetic communication with an insulated substrate; obtaining corrosion related data by means of the thermal imaging devices; and communicating the corrosion related data to an operator.

A system for detecting corrosion under insulation is also provided, the system including at least: one or more thermal imaging devices disposed in electromagnetic communication with an insulated substrate; a means for obtaining corrosion related data using the thermal imaging devices; and a means for communicating the corrosion related data to an operator.

BRIEF DESCRIPTION OF THE DRAWINGS

The embodiments disclosed herein will be better understood, and numerous objects, features, and advantages made apparent to those skilled in the art by referencing the accompanying drawings.

DETAILED DESCRIPTION OF VARIOUS EXAMPLE EMBODIMENTS

The description that follows includes exemplary systems, methods, and techniques that encompass several different embodiments of the presently inventive subject matter. However, it will be understood by those of ordinary skill in the pertinent arts that the disclosed embodiments may be practiced in the absence of one or more of the specific details described herein. In other instances, well-known manufacturing equipment, protocols, structures and techniques have not been shown or described in detail in order to avoid obfuscation in the description.

Embodiments of the inventive subject matter integrate equipment, automation, and algorithms to form a method for identifying wet thermal insulation by scanning multiple locations along insulated piping, tanks, or other manufacturing equipment. In various embodiments, such scans can occur individually, sequentially, or simultaneously, with the results then being stored and comparatively analyzed.

Further embodiments comprise tracking the approximate time of exposure to moisture, prediction of the corrosion rates for underlying insulated metal substrates, and measuring wall thicknesses along predetermined random portions of the metal substrate. Some embodiments of the invention utilize advanced infrared imaging video cameras to detect characteristic signatures of wet thermal traits on process equipment.

Figure 1A:
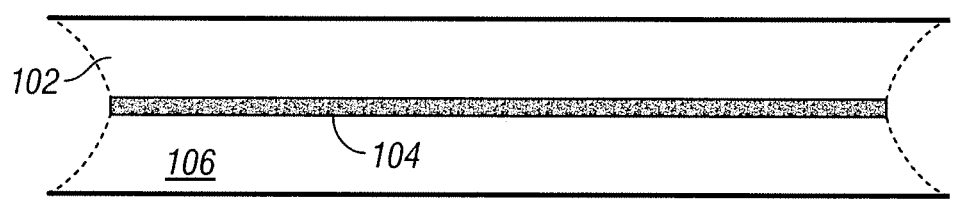
FIGS. 1A and 1B are cross sectional views of a subsection of insulated piping, according to example embodiments.
Figure 1B:
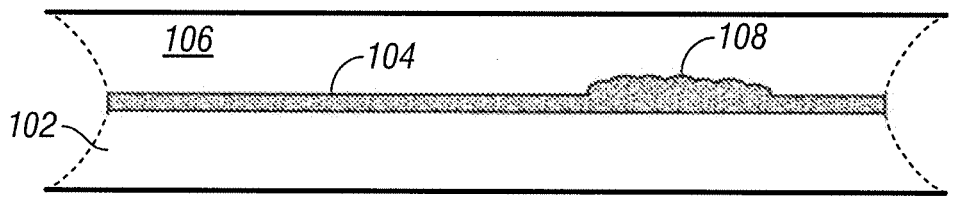

FIGS. 1A and 1B are cross sectional views of a subsection of insulated pipe, according to one example embodiment. The subsection of insulated piping in FIG. 1A comprises an insulated portion 102 disposed in communication with a portion of a metal tubular 106. Over time, a plurality of factors have has caused formation of an intervening corrosive layer 104.

Metal tubular 106 is comprised of one or more metallic materials, or another non-metallic material susceptible to corrosion, for example, aluminum, titanium, stainless steel, carbon steel, copper, brass, bronze, etc. Insulation 102 is comprised of any of a plurality of appropriate insulation materials. Common examples of insulation include blankets, loose fill, and low-density foams, each of which work by limiting air movement; fiberglass; cellulose; polyicynene; and expanded polystyrene. Some foam insulators, such as polyisocyanurate, polyurethane, and extruded polystyrene, are filled with gases that provide additional resistance to heat flow, and even ambient air can serve as an effective insulator, because it eliminates convection and has low conduction.

Insulation 102 can also comprise a reflective insulation material, which works by reducing the amount of energy that travels in the form of radiation, or by dividing a region or space into a number of smaller regions in order to reduce convection.

Examples of corrosive substances 104 include organic and inorganic scale, rust, liquids and other fluid condensates caused by rain water, leakage, cleaning fluids, and sweating resulting from elevated or cycling temperature gradients.

In one particular though non-limiting application, a metal tubular used in a factory experiences high inner surface temperatures (e.g., 75° C.) generated by an associated process flow. The temperature of the outer surface of the insulation, however, is normally much cooler. Water, or other corrosive fluids retained in the insulating layer cause corrosion of the metal tubular. The associated temperature gradient results in concentration of corrosive species at the surface of the metal tubular, at the insulation/tubular interface, the result of which is a localized environment in which corrosion can develop (e.g., pitting, scale, etc.), which can quickly lead to a flaw in the tubing 108. The presence of the liquid in the insulating layer causes improved heat transfer and results in higher temperatures at the outer surface of the insulating layer. Such areas are observed as "hot spots" which are indicative of potential corrosive sites.

According to a presently preferred embodiment, damaged tubing 108 and corrosive substance 104 are monitored and marked for physical inspection by a combination of one or more CUI thermal imaging devices and associated monitors and controllers, aspects of which are discussed in detail in the following sections.

CUI Thermal Imaging Device(s)

Figure 2A:
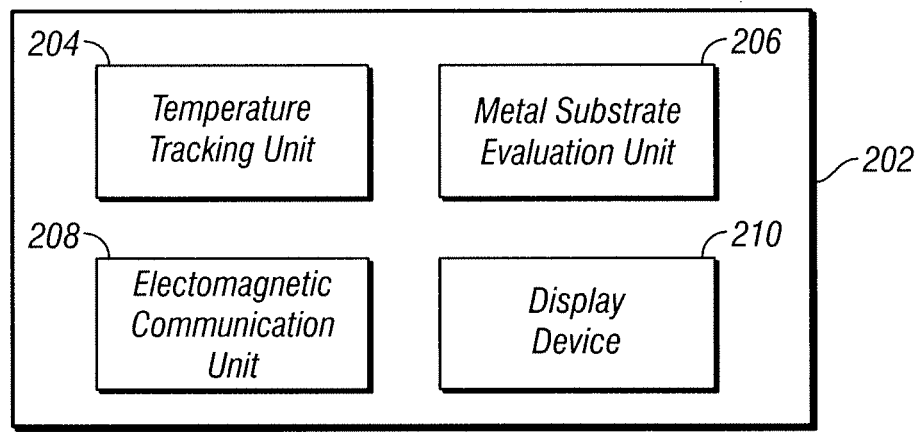
FIG. 2A is a block diagram of a CUI thermal imaging device, according to example embodiments.

FIG. 2A is a block diagram of a CUI thermal imaging device, according to one example embodiment. Some embodiments of the CUI thermal imaging device detect phenomena associated with localized corrosion, and either present the detection information to a display for viewing by the user, and/or transmit and receive various communications to and from CUI monitor(s) that are either affixed to the insulated substrates or remotely positioned in such a manner as to permit scanning of the installation. Further embodiments of the CUI thermal imaging device display data regarding substantive CUI information, including the time-of-wetness associated with the thermal insulation, real time imaging of locations where a metal substrate wall thickness has been reduced, and the damage rate of existing CUI.

An example CUI thermal imaging device 202 block diagram depicted in FIG. 2A comprises a temperature tracking unit 204, a metal substrate evaluation unit 206, an electromagnetic (EM) communication unit 208, and a display device 210. The temperature tracking unit 204 compiles data received from the CUI monitors' temperature measuring unit(s) and calculates the expected level of liquid contamination and the propensity for CUI within a certain area of a metal substrate. For example, a plurality of CUI monitors 212 affixed to or disposed in proximity of a series of plant tubulars can detect high inner-pipe temperatures resulting from process flow moving through the tubular housings. As mentioned, however, lower external temperatures can lead to significant temperature gradients at or near the interface of the insulation and the pipe, thereby creating a significant amount of concentration of corrosive species which results in faster CUI development. Embodiments of the temperature tracking unit 204 calculate these detected temperature gradients throughout the pipe and identify areas that are at risk of CUI due to heavy liquid contamination.

Likewise, rainwater, cleaning fluids, seeping process flow, etc., can migrate into the void space formed between a tubular and associated insulation, thereby creating a localized environment where pitting or scale, etc., can attack the integrity of the tubular body. In such cases, electromagnetic communication unit 208 directs an infrared beam or the like at the structure, thereby revealing sites where corrosion is likely to form under the insulation. Display device 210 indicates to operators various physical factors associated with hot spots or the like (for example, as might be obtained from temperature tracking unit 204), so that operators can mark the site for physical inspection. In some embodiments, associated insulation is removed, and metal substrate evaluation unit 206 further scans the installation for predetermined indicia regarding the condition of the tubular.

For example, CUI thermal imaging device 202 can be used to analyze and evaluate metal substrate reduction data received from the CUI monitor's metal substrate evaluation unit 206. This information is used to identify areas of the insulated metal substrate most at risk of significant corrosion and deterioration. Corrosion such as pitting and scaling can be caused by chemical flow seeping out of a tubular and migrating along a surface of the metal substrate, introduction of liquids from outside the installation into the void formed between the insulation and the metal substrate interface, etc. Once the metal substrate evaluation unit 206 has compiled the received data, EM communications unit 208 is utilized to monitor the reduced or damaged area of the metal substrate.

In example embodiments of the CUI thermal imaging device, the EM communications unit 208 communicates with the CUI monitor(s) 212 via a variety of communication methods. For example, transmitting and receiving of CUI data can be achieved using radio waves, SONET, Bluetooth, etc. Further embodiments of the EM communications unit 208 detect and monitor characteristic thermal traits along insulated piping, tanks, or other manufacturing equipment using infrared imaging, radiographic, ultrasonic, etc. technologies. In such manner, the system allows for a non-destructive method of inspecting, testing, and monitoring existing and potential CUI locations. For example, if data received from the CUI monitors 212 indicates a concentrated area of condensation at a specific location along insulated piping, the CUI thermal imaging device 202 can monitor that area using infrared imaging technology. In contrast, known prior art methods would likely have involved destruction of the affected region, or downtime and removal of the insulation for direct inspection.

Embodiments of the display device 210 allow information received from CUI monitors to be read and evaluated prior to taking steps to remedy any existing or potential CUI damage.

CUI Monitor(s)

In some embodiments, one or more CUI monitors are strategically placed proximate to a plurality of insulated piping, tanks, or other manufacturing equipment, and scan the installation for various predetermined thermal and physical conditions. For example, wet/dry insulation, damaged or missing insulation, and metal substrate wall reduction can all be detected by the CUI monitors. In further embodiments, CUI monitors transmit and receive data to and from other CUI monitors. Communication between CUI monitors allows for high risk areas to be monitored by one or more CUI monitors. In other embodiments, the CUI monitors are disposed in electronic or signal communicate with one or more CUI thermal imaging devices. Communication between CUI monitors, or between CUI monitors and CUI thermal imaging devices, can employ any suitable wireless or wired connection technology, such as Ethernet, radio waves, SONET, Bluetooth, etc. In further embodiments, a single CUI monitor can scan and monitor an entire area of insulated piping, tanks, or other manufacturing equipment.

Figure 2B:
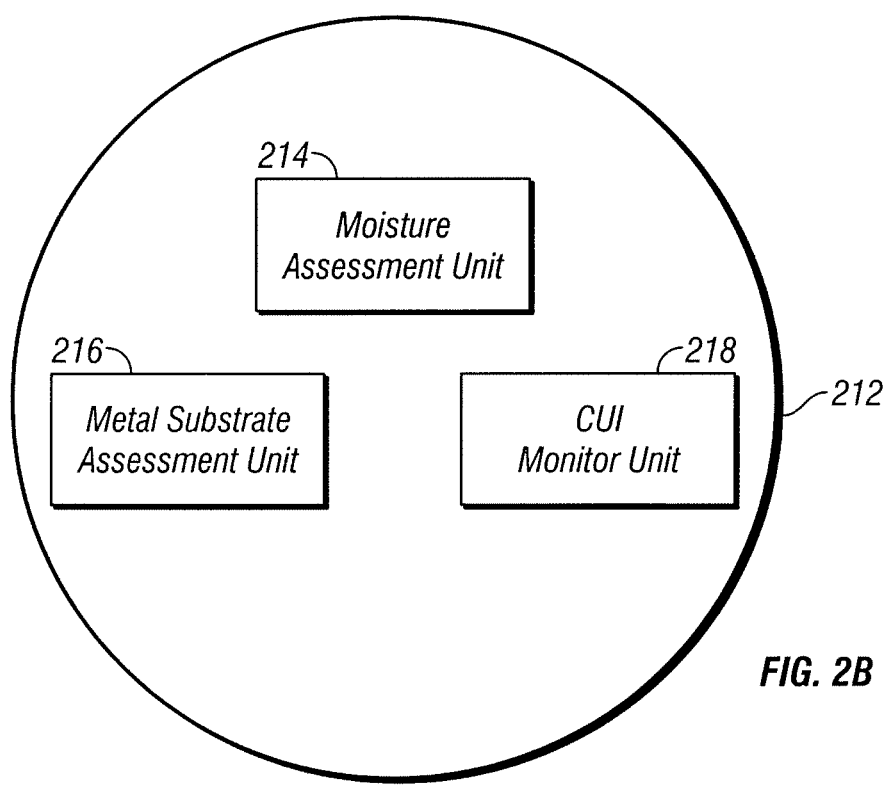
FIG. 2B is a block diagram of a CUI monitor, according to example embodiments.

The CUI monitor 212 block diagram depicted in FIG. 2B comprises a moisture assessment unit 214, a metal substrate assessment unit 216, and a CUI monitor unit 218. Example embodiments of the moisture assessment unit 214 identify predetermined temperature gradients between insulation and metal substrates. Further embodiments of the moisture assessment unit 214 identify wet and dry thermal insulation, and track the time of wetness. For example, a CUI monitor's moisture assessment unit 214 can detect accumulated condensation at the insulation/metal substrate interface by examination of the thermal insulation. If the insulation is wet near the interface, there is an expectation of condensation, thus increasing the CUI potential. In some embodiments, the data gathered by the moisture assessment unit 214 is subsequently transmitted to a CUI thermal imaging device 202 for evaluation and further analysis. Analysis of this data provides information needed for assessing the rate of attack and/or cumulative damage as a result of CUI.

A number of factors, including CUI, can result in the deterioration of metal substrate walls. Wall reduction will eventually result in significant damage to the substrate, and halt the manufacturing process while repairs are made. The metal substrate unit 216 scans and monitors the plane of the substrate in search of wall thickness reduction. For example, embodiments of a metal substrate unit 216 can be preprogrammed with data containing standard wall thickness of a particular metal substrate. If the standard wall thickness is no longer present in a certain area, the metal substrate unit will detect it by differentiating between thermal signatures at various points along the substrate. Embodiments of the metal substrate unit 216 employ a variety of corrosion and thermal detection technology, such as infrared imaging, radiographic, ultrasonic, etc. Following detection of a deleterious condition, the metal substrate unit 216 transmits associated data to a CUI thermal imaging device 202 for evaluation and analysis.

The CUI monitor unit 218 identifies existing and potential CUI along a substrate before it becomes damaging to the host material. For example, the CUI monitor unit 218 can detect corrosive qualities at the metal substrate/insulation interface, or within or upon an inner surface of the substrate, using EM technology such as infrared imaging, radiographic, ultrasonic, etc. Certain embodiments of the CUI monitor unit 218 subsequently transmit the gathered information to CUI thermal imaging device 202 for further analysis.

Optimally, CUI thermal imaging device 202 and CUI monitor 212 operate cooperatively, utilizing the methods and techniques described above to locate existing or potential areas along the insulated piping for CUI development. For example, a CUI monitor 212 can be programmed to monitor and scan a plant region suspected of providing a favorable environment for formation of CUI. During examination, the embedded moisture assessment unit detects condensation in the region. The condensation data is wirelessly transmitted to an associated CUI thermal imaging device 202, which then scans the region continuously until necessary preventative actions can be taken.

The foregoing specification is provided for illustrative purposes only, and is not intended to describe all possible aspects of the present invention. Moreover, while the invention has been shown and described in detail with respect to several exemplary embodiments, those of ordinary skill in the pertinent arts will appreciate that minor changes to the description, and various other modifications, omissions and additions may also be made without departing from either the spirit or scope thereof.

The invention claimed is:

1. A method of detecting corrosion under insulation, said method comprising:
    disposing one or more thermal imaging devices in electromagnetic communication with an insulated substrate;
    disposing said one or more thermal imaging devices in communication with an associated corrosion under insulation monitor comprising a moisture assessment unit, a metal substrate assessment unit, and a CUI monitor unit, strategically located proximate to said insulation at a plurality of locations;
    scanning multiple location subsections of said insulated substrate simultaneously for temperature gradients experienced by said insulated substrate as a result of a process flow associated with said insulated substrate with said one or more thermal imaging devices;
    using said one or more thermal imaging devices to scan multiple location subsections of said insulated substrate simultaneously for temperature gradients experienced by said insulated substrate as a result of a process flow associated with said insulated substrate;
    obtaining corrosion related data, including said temperature gradients, by transmitting said corrosion related data to said corrosion under insulation monitor by means of said thermal imaging devices; and
    communicating said corrosion related data to an operator via said CUI monitor unit.

2. The method of detecting corrosion under insulation of claim 1, said method further comprising:
    disposing said one or more thermal imaging devices in electromagnetic communication with a metallic substrate.

3. The method of detecting corrosion under insulation of claim 1, said method further comprising:
    disposing said one or more thermal imaging devices in electromagnetic communication with a non-metallic substrate conducive to the formation of corrosion.

4. The method of detecting corrosion under insulation of claim 1, said method further comprising:
    disposing one or more of said thermal imaging devices wherein at least one of said thermal imaging devices is an infrared imaging camera in electromagnetic communication with said insulated substrate.

5. The method of detecting corrosion under insulation of claim 1, said method further comprising:
    disposing said one or more thermal imaging devices in electromagnetic communication with said insulated substrate; and
    scanning a plurality of insulated substrate regions sequentially, by means of said one or more thermal imaging devices.

6. The method of detecting corrosion under insulation of claim 1, said method further comprising:
    obtaining corrosion related data wherein said corrosion related data comprises corrosion pitting data by means of said thermal imaging devices.

7. The method of detecting corrosion under insulation of claim 1, said method further comprising:
    obtaining data evidencing the presence of a concentration of a corrosive species comprising organic scale by means of said thermal imaging devices.

8. The method of detecting corrosion under insulation of claim 1, said method further comprising:

obtaining data evidencing the presence of a concentration of a corrosive species comprising inorganic scale by means of said thermal imaging devices.

9. The method of detecting corrosion under insulation of claim 1, said method further comprising:

obtaining corrosion related data wherein said corrosion related data comprises data relating to at least one of a time of exposure to wetness; and prediction of a rate of corrosion formation, by means of said thermal imaging devices.

10. The method of detecting corrosion under insulation of claim 1, said method further comprising:

disposing said thermal imaging device in wireless communication with an associated corrosion under insulation monitor.

11. A system for detecting corrosion under insulation, said system comprising:

one or more thermal imaging devices disposed in electromagnetic communication with an insulated substrate;

said one or more thermal imaging devices disposed in communication with one or more associated corrosion under insulation monitor comprising a moisture assessment unit, a metal substrate assessment unit, and a CUI monitor unit, strategically located proximate to said insulation at a plurality of locations, wherein said one or more thermal imaging devices scan multiple location subsections of said insulated substrate simultaneously for temperature gradients experienced by said insulated substrate as a result of a process flow associated with said insulated substrate;

a means for obtaining corrosion related data, including said temperature gradients, by transmitting said corrosion related data collected by said thermal imaging devices to said corrosion under insulation monitor; and a means for communicating said corrosion related data to an operator.

12. The system for detecting corrosion under insulation of claim 11, said system further comprising:

said one or more thermal imaging devices in electromagnetic communication with a metallic substrate.

13. The system of detecting corrosion under insulation of claim 11, said system further comprising:

said one or more thermal imaging devices in electromagnetic communication with a non-metallic substrate conducive to the formation of corrosion.

14. The system of detecting corrosion under insulation of claim 11, said system further comprising:

one or more thermal imaging devices comprising at least one infrared imaging cameras in electromagnetic communication with said an insulated substrate.

15. The system of detecting corrosion under insulation of claim 11, said system further comprising:

said one or more thermal imaging devices in electromagnetic communication with said insulated substrate; and a means for scanning a plurality of insulated substrate regions sequentially, using said one or more thermal imaging devices.

16. The system of detecting corrosion under insulation of claim 11, said system further comprising:

a means for obtaining corrosion related data wherein said corrosion related data comprises corrosion pitting data using said thermal imaging devices.

17. The system of detecting corrosion under insulation of claim 11, said system further comprising:

a means for obtaining data evidencing the presence of a concentration of a corrosive species comprising organic scale using said thermal imaging devices.

18. The system of detecting corrosion under insulation of claim 11, said system further comprising:

a means for obtaining data evidencing the presence of a concentration of a corrosive species comprising inorganic scale using said thermal imaging devices.

19. The system of detecting corrosion under insulation of claim 11, said system further comprising:

a means for obtaining corrosion related data wherein said corrosion related data comprises data relating to at least one of a time of exposure to wetness; and prediction of a rate of corrosion formation.

20. The system of detecting corrosion under insulation of dam 11, said system further comprising:

a thermal imaging device disposed in wireless communication with an associated corrosion under insulation monitor.

* * * * *